(12) United States Patent
Kogawa et al.

(10) Patent No.: US 12,421,355 B2
(45) Date of Patent: Sep. 23, 2025

(54) BIODEGRADABLE BLOCK COPOLYMER

(71) Applicant: Toray Industries, Inc., Tokyo (JP)

(72) Inventors: Taisuke Kogawa, Otsu (JP); Masaki Fujita, Otsu (JP); Yuichi Koyamatsu, Otsu (JP); Kazuhiro Tanahashi, Otsu (JP); Kazuyuki Kidoba, Otsu (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 17/040,809

(22) PCT Filed: Jan. 25, 2019

(86) PCT No.: PCT/JP2019/002391
§ 371 (c)(1),
(2) Date: Sep. 23, 2020

(87) PCT Pub. No.: WO2019/187569
PCT Pub. Date: Oct. 3, 2019

(65) Prior Publication Data
US 2021/0002432 A1    Jan. 7, 2021

(30) Foreign Application Priority Data

Mar. 30, 2018  (JP) ............................... 2018-067452

(51) Int. Cl.
*C08G 81/00*    (2006.01)
*A61L 24/04*    (2006.01)
*C09D 171/02*   (2006.01)

(52) U.S. Cl.
CPC ............ *C08G 81/00* (2013.01); *A61L 24/046* (2013.01); *C09D 171/02* (2013.01); *C08G 2150/00* (2013.01)

(58) Field of Classification Search
CPC ..... A61L 17/12; C08G 63/664; C08G 63/668; C08G 63/672
See application file for complete search history.

(56) References Cited

U.S. PATENT DOCUMENTS

| | | | |
|---|---|---|---|
| 4,826,945 A | 5/1989 | Cohn et al. | |
| 5,578,325 A * | 11/1996 | Domb ................... | A61K 9/1635 424/497 |
| 10,300,019 B2 | 5/2019 | Steendam et al. | |
| 2002/0161134 A1 | 10/2002 | Kim et al. | |
| 2005/0281866 A1 * | 12/2005 | Jarrett ................... | A61L 24/043 424/448 |
| 2006/0034888 A1 | 2/2006 | Pacetti et al. | |
| 2013/0253136 A1 | 9/2013 | Tanahashi et al. | |
| 2014/0018505 A1 | 1/2014 | Fujita et al. | |
| 2015/0093444 A1 * | 4/2015 | Zhang ................... | A61K 47/34 424/501 |
| 2018/0028496 A1 * | 2/2018 | Taratula ............... | A61K 31/409 |

FOREIGN PATENT DOCUMENTS

| | | |
|---|---|---|
| CN | 103073730 B | 7/2015 |
| JP | 1-195862 | 8/1989 |
| JP | 2001-261838 | 9/2001 |
| JP | 4822222 | 11/2011 |
| JP | 5209192 | 6/2013 |
| JP | 2014139264 A * | 7/2014 |
| JP | 6094219 | 3/2017 |
| JP | 2017-141477 | 8/2017 |
| WO | 2012/77776 | 6/2012 |

OTHER PUBLICATIONS

Pourcelle et al. "Light Induced Functionalization of PCL-PEG Block Copolymers for the Covalent Immobilization of Biomolecules", Biomacromolecules 2009, 10, 966-974 (Year: 2009).*

Braunova et al. "Degradation Behavior of Poly(Ethylene Glycol) Diblock and Multiblock Polymers With Hydrolytically Degradable Ester Linkages", Collect. Czech. Chem. Commun. (vol. 69) (Year: 2004).*

The Extended European Search Report dated Dec. 8, 2021, of counterpart European Application No. 19777608.1.

T. Wang et al., "Synthesis of poly(p-dioxanone)-based block copolymers in supercritical carbon dioxide," *Colloid & Polymer Science*, Springer Verlag, Heidelberg, DE, vol. 292, No. 10, pp. 2497-2508, Jun. 7, 2014.

M.R. Nabid et al., "Self-assembled micelles of well-defined pentaerythritol-centered amphiphilic ABstar-block copolymers based on PCL and PEG for hydrophobic drug delivery," *Polymer*, Elsevier, Amsterdam, NL, vol. 52, No. 13, pp. 2799-2809, Apr. 26, 2011.

Messmore, Benjamin W. et al., "Synthesis, Self-Assembly, and Characterization of Supramolecular Polymers from Electroactive Dendron Rodcoil Molecules," *Journal of the American Chemical Society*, 126 (44): 14452-14458, Oct. 19, 2004. https://doi.org/10.1021/ja049325w.

Andreas Wurm et al., "Crystallization of poly(&-caprolactone)/MWCNT composites: A combined SAXS/WAXS, electrical and thermal conductivity study," Elsevier, Polymer, vol. 55, Issue 9, pp. 2220-2232, Apr. 2014.

* cited by examiner

*Primary Examiner* — James W Rogers
(74) *Attorney, Agent, or Firm* — DLA Piper LLP (US)

(57) ABSTRACT

A biodegradable block copolymer has high conformability and excellent degradability. The block copolymer including a polyalkylene glycol block and a polyhydroxyalkanoic acid block, wherein the mass ratio of the polyalkylene glycol block with respect to the total mass is 10 to 60%; the carbonyl carbon has a carbon nuclear relaxation time $T1\rho$ of not more than 20 ms; and the block copolymer satisfies Equation (1): $\chi = \chi 1 \times \chi 2 > 20$ (1) $\chi 1$: crystallization rate of the polyalkylene glycol block; $\chi 2$: crystallization rate of a poly-A block, wherein A represents, among the repeat units contained in the polyhydroxyalkanoic acid block, a repeat unit whose homopolymer composed of the same repeat units has a highest crystallization rate.

24 Claims, No Drawings

BIODEGRADABLE BLOCK COPOLYMER

TECHNICAL FIELD

This disclosure relates to a biodegradable block copolymer having high conformability and excellent degradability.

BACKGROUND

Biodegradable polymers are widely used for medical uses such as medical materials, vascular embolization materials, suture threads and DDS carriers.

Medical coating materials to be implanted into the body, since they are placed in the body, need to be non-toxic, and to be finally degraded and excreted to the outside of the body.

Reported examples of such medical materials using biodegradable polymers having excellent degradability include a polyether glycol-based biodegradable block copolymer material (JP 01-195862 A) and a coating for implantable medical devices, which coating comprises a block copolymer containing a polyhydroxy acid block and a biocompatible polymer block (JP 4822222 B).

Further, an artificial skin prepared by processing a multiblock copolymer comprising a biodegradable polymer block and a water-soluble polymer block into a porous sheet shape (JP 5209192 B) and a vascular embolization material prepared by processing the copolymer into a particle shape (JP 6094219 B) have been reported.

A medical coating material to be implanted in the body is required to have not only degradability, but also conformability that allows the material to conform to movement of a living body. Each block copolymer described in JP 01-195862 A and JP 4822222 B is a triblock polymer containing polyhydroxyalkanoic acid blocks placed at both ends of a polyalkylene glycol block (a block copolymer represented by General Formula (A)), or a multiblock polymer prepared by multimerizing the triblock polymer (the block copolymer represented by General Formula (B) or (C)). Although polymers based on such a triblock polymer structure have excellent degradability, they have poor conformability so that they need further improvement for use as medical coating materials to be implanted in the body.

Each block polymer described in JP 5209192 B and JP 6094219 B (a block copolymer represented by General Formula (D)) contains a low molecular weight compound as a linker molecule in a polyhydroxyalkanoic acid block and, therefore, the molecule has a decreased crystallinity, resulting in a decreased tensile strength. Thus, the conformability of the polymer is unsatisfactory when the polymer is processed into a sheet shape.

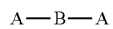 (A)

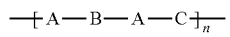 (B)

 (C)

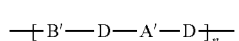 (D)

In the Formulae (A) to (D), A represents a polyhydroxyalkanoic acid block; B represents a polyalkylene glycol block; C represents a linker molecule containing two or more carboxyl groups; and D represents C or a single bond. A' represents A or a block of two or more As linked to each other through C(s) (with the proviso that the molecule necessarily contains a block of two or more As linked to each other through C(s)). B' represents B or a block of two or more Bs linked to each other through C(s) (with the proviso that the molecule necessarily contains a block of two or more Bs linked to each other through C(s)). n represents an integer of 1 or more.

It could, therefore, be helpful to provide a biodegradable block copolymer having high conformability and excellent degradability.

SUMMARY

We Thus Provide:

(1) A block copolymer comprising a polyalkylene glycol block and a polyhydroxyalkanoic acid block,
wherein
the mass ratio of the polyalkylene glycol block with respect to the total mass is 10 to 60%;
the carbonyl carbon has a carbon nuclear relaxation time T1ρ of not more than 20 ms; and
the block copolymer satisfies Equation (1):

$$\chi = \chi_1 \times \chi_2 > 20 \qquad (1)$$

$\chi_1$: crystallization rate of the polyalkylene glycol block;
$\chi_2$: crystallization rate of a poly-A block, wherein A represents, among the repeat units contained in the polyhydroxyalkanoic acid block, a repeat unit whose homopolymer composed of the same repeat units has a highest crystallization rate.

(2) The block copolymer according to (1), wherein the polyhydroxyalkanoic acid block comprises a repeat unit derived from a monomer selected from the group consisting of lactic acid, glycolic acid and caprolactone.

(3) The block copolymer according to (1) or (2), wherein the mass ratio of the repeat unit derived from caprolactone with respect to the total mass of the block copolymer is 20 to 80%.

(4) The block copolymer according to (1), wherein the weight average molecular weight of the polyalkylene glycol block is 7,000 to 170,000.

(5) The block copolymer according to any one of (1) to (4), which is represented by General Formula (I):

 (I)

wherein
A represents a polyhydroxyalkanoic acid block; B represents a polyalkylene glycol block; C represents a linker molecule containing two or more carboxyl groups; and D represents C or a single bond;

B' represents B or a block of two or more Bs linked to each other through C(s) (with the proviso that the molecule necessarily contains a block of two or more Bs linked to each other through C(s)); and n represents an integer of 1 or more.

(6) The block copolymer according to (5), wherein A is represented by General Formula (II):

(II)

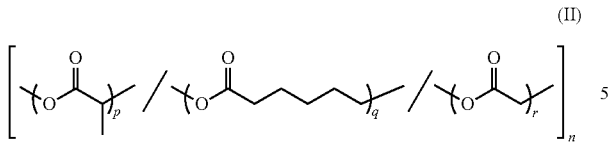

wherein p, q, r, and n each represent an integer of 1 or more.
(7) The block copolymer according to (5), wherein A is represented by General Formula (III):

(III)

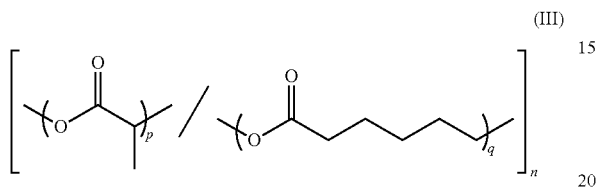

wherein p, q, and n each represent an integer of 1 or more.
(8) The block copolymer according to (5), wherein B is represented by General Formula (IV):

(IV)

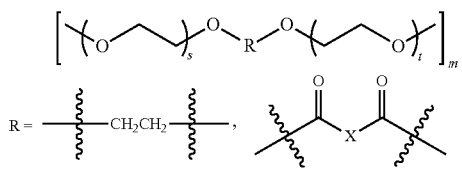

wherein s, t, and m each represent an integer of 1 or more, and X represents a structure derived from a linker molecule containing two or more carboxyl groups (with the proviso that the molecule necessarily contains B containing X).
(9) A medical material comprising: the block copolymer according to any one of (1) to (8); and a molded article to be coated with the block copolymer.
(10) A block copolymer comprising a polyalkylene glycol block and a polyhydroxyalkanoic acid block,
wherein
the mass ratio of the polyalkylene glycol block with respect to the total mass is 15 to 60%; and
the block copolymer satisfies Equation (1):

$$\chi = \chi 1 \times \chi 2 > 20 \quad (1)$$

$\chi 1$: crystallization rate of the polyalkylene glycol block;
$\chi 2$: crystallization rate of a poly-A block, wherein A represents, among the repeat units contained in the polyhydroxyalkanoic acid block, a repeat unit whose homopolymer composed of the same repeat units has a highest crystallization rate.
(11) The block copolymer according to (10), wherein the polyhydroxyalkanoic acid block comprises a repeat unit derived from a monomer selected from the group consisting of lactic acid, glycolic acid and caprolactone.
(12) The block copolymer according to (10) or (11), wherein the mass ratio of the repeat unit derived from caprolactone with respect to the total mass of the block copolymer is 20 to 80%.
(13) The block copolymer according to (10), wherein the weight average molecular weight of the polyalkylene glycol block is 7,000 to 170,000.

(14) The block copolymer according to any one of (10) to (13), which is represented by General Formula (I):

(I)

wherein
A represents a polyhydroxyalkanoic acid block; B represents a polyalkylene glycol block; C represents a linker molecule containing two or more carboxyl groups; and D represents C or a single bond;
B' represents B or a block of two or more Bs linked to each other through C(s) (with the proviso that the molecule necessarily contains a block of two or more Bs linked to each other through C(s)); and
n represents an integer of 1 or more.
(15) The block copolymer according to (14), wherein A is represented by General Formula (II):

(II)

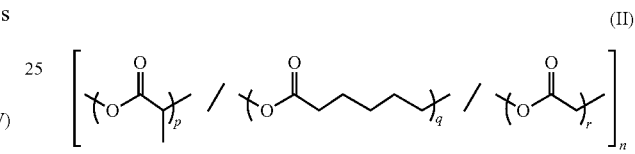

wherein p, q, r, and n each represent an integer of 1 or more.
(16) The block copolymer according to (14), wherein A is represented by General Formula (III):

(III)

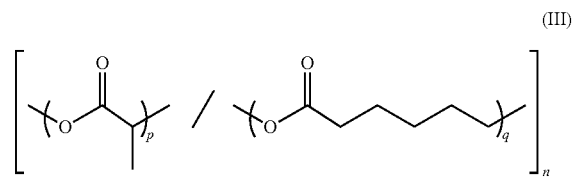

wherein p, q, and n each represent an integer of 1 or more.
(17) The block copolymer according to (14), wherein B is represented by General Formula (IV):

(IV)

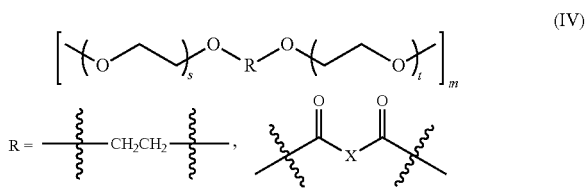

wherein s, t, and m each represent an integer of 1 or more, and X represents a structure derived from a linker molecule containing two or more carboxyl groups (with the proviso that the molecule necessarily contains B containing X).
(18) A medical material comprising: the block copolymer according to any one of (10) to (17); and a molded article to be coated with the block copolymer.

By controlling the crystallization rates and the mass ratios of the polyalkylene glycol block and the polyhydroxyalkanoic acid block in the block copolymer, our block copolymer can have conformability enough to withstand movement of a living body, and degradability enough to appropriately undergo degradation after playing the role in a living body.

DETAILED DESCRIPTION

Our block copolymer comprises a polyalkylene glycol block and a polyhydroxyalkanoic acid block,
wherein
the mass ratio of the polyalkylene glycol block with respect to the total mass is 10 to 60%;
the carbonyl carbon has a carbon nuclear relaxation time T1ρ of not more than 20 ms; and
the block copolymer satisfies Equation (1):

$$\chi = \chi_1 \times \chi_2 > 20 \qquad (1)$$

$\chi_1$: crystallization rate of the polyalkylene glycol block;
$\chi_2$: crystallization rate of a poly-A block, wherein A represents, among the repeat units contained in the polyhydroxyalkanoic acid block, a repeat unit whose homopolymer composed of the same repeat units has a highest crystallization rate.

The biodegradability means a property that allows degradation in vivo. The biodegradable polymer means a polymer having such a property. The term "biodegradability" is interchangeably used with terms such as bioabsorbability and biocompatibility. The biodegradable polymer is not limited as long as it is degraded in vivo, and examples thereof include polylactic acid, polyglycolic acid, poly(ε-caprolactone), and polydioxanone. A plurality of materials such as a lactic acid-glycolic acid copolymer, glycolic acid-ε-caprolactone copolymer, or lactic acid-ε-caprolactone copolymer may be used. As long as the desired effect is not deteriorated, the biodegradable polymer may be their mixture, or a mixture with a water-soluble polymer such as polyalkylene glycol.

The polyalkylene glycol means a polymer prepared by polymerization of two or more kinds of alkylene glycols, and examples of the polymer include those containing two or more repeat units derived from alkylene glycols such as ethylene glycol, propylene glycol, oxyethylene glycol dimethyl ether, polyoxypropylene glycol monobutyl ether, and polyoxypropylene glycol diacetate.

The polyhydroxyalkanoic acid is a polymer prepared by polymerizing one or more kinds of hydroxyalkanoic acids, and examples of the hydroxyalkanoic acids include 2-hydroxypropionic acid (lactic acid), 2-hydroxybutanoic acid, 2-hydroxypentanoic acid, 2-hydroxyhexanoic acid, 3-hydroxybutanoic acid (3-hydroxybutyric acid), 3-hydroxypentanoic acid (3-hydroxyvaleric acid), 3-hydroxyhexanoic acid, 3-hydroxyheptanoic acid, 3-hydroxyoctanoic acid, 3-hydroxynonanoic acid, 3-hydroxydecanoic acid, 4-hydroxypentanoic acid, 4-hydroxyhexanoic acid, 4-hydroxyheptanoic acid, 4-hydroxyoctanoic acid, 5-hydroxyhexanoic acid, 5-hydroxyheptanoic acid, 6-hydroxyheptanoic acid, 6-hydroxyoctanoic acid, 8-hydroxynonanoic acid, 8-hydroxydecanoic acid, 9-hydroxydecanoic acid, 9-hydroxyundecanoic acid, 10-hydroxyundecanoic acid, 10-hydroxydodecanoic acid, 11-hydroxydodecanoic acid, and 12-hydroxytridecanoic acid.

The mass ratio of the polyalkylene glycol block with respect to the total mass of the block copolymer means a value obtained by NMR measurement as described in Measurement Example 1. For controlling the conformability and the degradability within preferred ranges, the mass ratio of the polyalkylene glycol block with respect to the total mass of the block copolymer is preferably 10 to 60%, more preferably 15 to 60%, still more preferably 20 to 50%, most preferably 25 to 40%.

Since polyalkylene glycol is not degraded in vivo, the polyalkylene glycol has a weight average molecular weight of preferably not more than 170,000, more preferably not more than 100,000, still more preferably 50,000, for better excretion from the body. To provide reaction sites for the block structure within a preferred range, and to easily increase the weight average molecular weight of the block copolymer as a whole, the polyalkylene glycol has a weight average molecular weight of preferably not less than 7,000, more preferably not less than 8000, still more preferably not less than 10,000.

The mass ratio of the repeat unit derived from caprolactone with respect to the total mass of the block copolymer means a value obtained by NMR measurement as described in Measurement Example 1. To control the degradability and the Young's modulus within preferred ranges, the mass ratio of the repeat unit derived from polycaprolactone with respect to the total mass of the block copolymer is preferably 15 to 80%, more preferably 20 to 70%, still more preferably 25 to 60%, in terms of the mass ratio of polycaprolactone in the block copolymer.

Examples of the linker molecule containing two or more carboxyl groups include dicarboxylic acids, citric acid, and multi-branched polymers containing two or more carboxyl groups at branch ends; and acid halides, acid anhydrides, and esters of the dicarboxylic acids, citric acid, and multi-branched polymers. That is, the carboxylic acid groups may each be converted to an acid halide structure, ester structure, or acid anhydride structure. Examples of the dicarboxylic acids include oxalic acid, malonic acid, succinic acid, glutaric acid, adipic acid, pimelic acid, suberic acid, azelaic acid, sebacic acid, malic acid, tartaric acid, and dodecanedioic acid. Examples of the multi-branched polymers include hyperbranched polymers and dendrimers.

By preliminarily reacting the linker molecule with a polyalkylene glycol (having hydroxyl groups at both ends), production of a polyalkylene glycol (having carboxyl groups at both ends) or polyalkylene glycol (having a carboxyl group at one end) is possible, and these can be used as raw materials for producing a block copolymer.

It is known that the crystallinity of a block copolymer has a large impact on the mechanical strength of the block copolymer. Since a block copolymer having low crystallinity generally has a low Young's modulus, the crystallinity is preferably low for obtaining flexibility. However, when the crystallinity is extremely low, the tensile strength and the maximum-point elongation are low so that the block copolymer cannot withstand movement of a living body, resulting in poor conformability. In a block copolymer composed of a polyalkylene glycol and a polyhydroxyalkanoic acid, the crystallization rate of the block copolymer can be evaluated based on the value χ represented by Equation (1):

$$\chi = \chi_1 \times \chi_2. \qquad (1)$$

$\chi_1$: crystallization rate of the polyalkylene glycol block;
$\chi_2$: crystallization rate of a poly-A block, wherein A represents, among the repeat units contained in the polyhydroxyalkanoic acid block, a repeat unit whose homopolymer composed of the same repeat units has a highest crystallization rate.

As described later in Measurement Example 2, the value χ is determined from the value of the heat of fusion obtained by differential scanning calorimetry (DSC). The χ1 is determined according to Equation (2), and the χ2 is determined according to Equation (3).

χ1=(heat of fusion per unit weight of alkylene glycol residues in copolymer)/{(heat of fusion per unit weight of homopolymer composed only of alkylene glycol residues)×(weight fraction of alkylene glycol residues in copolymer)}×100    (2)

χ2=(heat of fusion per unit weight of A-residues in copolymer)/{(heat of fusion per unit weight of homopolymer composed only of A-residues)× (weight fraction of A-residues in copolymer)}× 100    (3)

The heat of fusion per unit weight of the homopolymer is determined as follows. The homopolymer is dissolved in chloroform at a weight concentration of 5%, and the resulting solution is transferred into a Teflon (registered trademark) petri dish, followed by allowing the solution to dry at normal pressure and room temperature for one day and night. The resulting product is dried under reduced pressure (100 Pa) at room temperature for one day and night to obtain a polymer film having a thickness of 100 μm±50 μm. The polymer film is taken into an aluminum PAN, and subjected to measurement using a differential scanning calorimeter (EXTAR 6000, manufactured by Seiko Instruments Inc.) by the DSC method according to Conditions A. The heat of fusion is read from the melting peak area in a graph.
Conditions A
 Instrument name: EXSTAR 6000 (manufactured by Seiko Instruments Inc.)
 Temperature conditions: 25° C.→250° C. (10° C./min)
 Standard substance: α-alumina To control the conformability of the block copolymer within a preferred range, the value χ, representing the crystallization rate of the block copolymer, is preferably not less than 20, more preferably not less than 500, still more preferably not less than 650, still more preferably not less than 800.

The mechanical strength of a block copolymer is known to be correlated also with the molecular mobility of the block copolymer. Since a block copolymer having high molecular mobility shows high tensile strength and high maximum-point elongation, the molecular mobility of the block copolymer is preferably high for obtaining a block copolymer having high conformability. The molecular mobility of the block copolymer can be evaluated by the carbon nuclear relaxation time T1ρ (ms) of the carbonyl carbon, obtained by the method using solid-state NMR measurement described later in Measurement Example 6.

To set the molecular mobility of the block copolymer within a preferred range, and control the conformability within a preferred range, the carbonyl carbon of the block copolymer has a carbon nuclear relaxation time T1ρ of preferably not more than 20 ms, more preferably not more than 18 ms, still more preferably not more than 16 ms.

When the block copolymer contains a lactic acid residue, to set the molecular mobility of the block copolymer within a preferred range, and control the conformability within a preferred range, the methyl group of the lactic acid residue has a carbon nuclear relaxation time T1ρ of preferably not more than 10.0 ms, more preferably not more than 8.0 ms, still more preferably not more than 6.0 ms. In the method described in Measurement Example 6, the peak derived from the methyl group of the lactic acid residue is found at 18±3 ppm.

When the block copolymer contains a caprolactone residue, to set the molecular mobility of the block copolymer within a preferred range, and control the conformability within a preferred range, the caprolactone residue has an α-carbon nuclear relaxation time T1ρ of preferably not more than 2.0 ms, more preferably not more than 1.8 ms, still more preferably not more than 1.6 ms; the methylene group at the 6-position of the caprolactone residue has a carbon nuclear relaxation time T1ρ of preferably not more than 1.5 ms, more preferably not more than 1.3 ms, still more preferably not more than 1.0 ms; and the methylene groups at the 3- to 5-positions of the caprolactone residue have a carbon nuclear relaxation time T1ρ of preferably not more than 2.5 ms, more preferably not more than 2.3 ms, still more preferably not more than 2.0 ms. The α-carbon of the caprolactone residue means the methylene group at the 2-position, and the methylene group at the 6-position means the methylene group adjacent to the oxygen atom. In the method described in Measurement Example 6, the peak derived from the α-carbon of the caprolactone residue is found at 34±2 ppm; the peak derived from the methylene group at the 6-position of the caprolactone residue is found at 66±1.9 ppm; and the peak derived from the methylene groups at the 3- to 5-positions of the caprolactone residue is found at 28±3 ppm.

When the block copolymer contains a lactic acid residue, and also contains a polyethylene glycol block, to set the molecular mobility of the block copolymer within a preferred range, and control the conformability within a preferred range, the methine group of the lactic acid residue and the methylene group of the ethylene glycol residue have a carbon nuclear relaxation time T1ρ of preferably not more than 8.0 ms, more preferably not more than 6.0 ms, still more preferably not more than 4.0 ms. In the method described in Measurement Example 6, the peak derived from the methine group of the lactic acid residue and the methylene group of the ethylene glycol residue is found at 70±1.9 ppm.

The Young's modulus, tensile strength, and maximum-point elongation are used as indices of the conformability. The excellent conformability means that the Young's modulus is low; the tensile strength is high; and the maximum-point elongation is high. More specifically, the excellent conformability means that the Young's modulus is not more than 100 MPa; the tensile strength is not less than 5.0 MPa; and the maximum-point elongation is not less than 600%.

The conformability of the block copolymer can be evaluated by the method described later in detail in Measurement Example 3. For the block copolymer to exhibit good conformability in vivo, the Young's modulus of the film composed of the block copolymer is preferably not more than 100 MPa, more preferably not more than 50 MPa, still more preferably not more than 10 MPa. The tensile strength is preferably not less than 5.0 MPa, more preferably not less than 7.0 MPa, still more preferably not less than 9.0 MPa. The maximum-point elongation is preferably not less than 600%, more preferably not less than 800%, still more preferably not less than 1000%.

The degradability of the block copolymer can be evaluated by a method such as the one described in Measurement Example 4. For the block copolymer to exhibit good degradability in vivo, the block copolymer weight (%) at Week 4 is preferably not more than 95%, more preferably not more than 90%, still more preferably not more than 85%. Here, the block copolymer weight (%) at Week 4 means a value determined according to the later-mentioned calculation equation represented by Equation 5.

Further, the degradability of the block copolymer can be evaluated by the method described in Measurement Example 7. For the block copolymer to exhibit good degradability in vivo, the block copolymer weight average molecular weight (%) at Week 4 is preferably not more than 85%, more preferably not more than 70%, still more preferably not more than 50%. The block copolymer weight average molecular weight (%) at Week 4 means a value determined according to the later-mentioned calculation equation represented by Equation 6.

The block copolymer can be molded into an arbitrary shape by dissolving the block copolymer in an organic solvent, and then drying the resulting solution. The organic solvent is not limited as long as the block copolymer can be dissolved therein. Examples of the organic solvent include chloroform, dichloromethane, acetone, tetrahydrofuran, ethyl acetate, N,N-dimethylformamide, N,N-dimethylacetamide, and dimethyl sulfoxide.

The weight average molecular weight of the block copolymer is preferably not less than 10,000 for improvement of the film formation property. There is not upper limit of the weight average molecular weight. However, for preventing problems in the production method caused by an increased viscosity, and for improving the moldability, the weight average molecular weight is preferably not more than 1,600,000, more preferably not more than 800,000, still more preferably not more than 400,000.

The weight average molecular weight can be determined by gel permeation chromatography (GPC). For example, it can be determined by the following method.

The block copolymer is dissolved in chloroform, and passed through a 0.45-μm syringe filter (DISMIC-13HP, manufactured by ADVANTEC) to remove impurities and the like, followed by measurement by GPC to calculate the weight average molecular weight of the block copolymer.

Apparatus name: Prominence (manufactured by Shimadzu Corporation)
Mobile phase: chloroform (HPLC grade) (manufactured by Wako Pure Chemical Industries, Ltd.)
Flow rate: 1 mL/min
Column: TSKgel (registered trademark) GMHHR-M (7.8 mm (diameter)×300 mm, manufactured by Tosoh Corporation)
Detector: UV (254 nm), RI
Column, detector temperature: 35° C.
Standard substance: polystyrene The block copolymer may be used as a coating material to coat a molded article. In this example, the block copolymer may be used as a medical material formed with the block copolymer and a molded article to be coated with the block copolymer. The molded article means an object molded into various shapes by a conventional method in accordance with the purpose. Examples of the molded article include membrane-like bodies (membranes, films, and sheets), plate-like bodies (boards), bar-like bodies (rods), cylindrical bodies (pipes and tubes), string-like bodies, net-like bodies (meshes), bag-like bodies, woven fabrics, and non-woven fabrics.

When the block copolymer is used as a coating material, the coating thickness means a value obtained by measuring the thickness of the block copolymer layer on a cross-section of a molded article by SEM. The value of the coating thickness of the block copolymer is set such that the conformability and pressure resistance are favorably controlled. The coating thickness achieved by the block copolymer is preferably 1 μm to 500 μm, more preferably 10 μm to 300 μm, still more preferably 20 μm to 200 μm.

When the molded article has water permeability, an anti-leakage function can be given by the coating with the block copolymer. The water permeability means the property which allows, upon application of a certain pressure on one surface of a molded article, flowing out of water from the opposite surface. The value calculated by dividing the amount of water (mL) that flows out upon application of a pressure of 16 kPa by the unit area ($cm^2$) and the unit time (min) is defined as the amount of permeated water and, when the amount of permeated water is larger than 0, the molded article is defined as having water permeability. For example, in a cylindrical body, the method of measuring the water permeability is a method according to ISO7198 in which the amount of water (mL) that flows out to the outside of the cylindrical body upon application of a pressure of 16 kPa to the inner surface of the cylindrical body is divided by the unit area ($cm^2$) and the unit time (min).

The kink diameter is as follows. After forming a loop with a cylindrical body or bar-like body, the diameter of the loop is gradually decreased. The minimum loop diameter at which no buckling occurs is the kink diameter. The kink diameter can be evaluated by the method described later in detail in Measurement Example 5. For better conformability to movement of the surrounding tissue after transplantation into the living body and easier transplantation to a curved portion, the kink diameter is preferably not more than 15 mm, more preferably not more than 10 mm. Taking use as an artificial blood vessel into account, the inner diameter of the cylindrical body is preferably 1 mm to 10 mm, more preferably 2 mm to 4 mm.

When the cylindrical body is composed of fibers, various organic fibers may be used therefor. From the viewpoint of water absorbability and deterioration resistance, polyesters are preferred. Examples of the polyesters include polyethylene terephthalate and polybutylene terephthalate. A copolymerized polyester prepared by copolymerizing a polyethylene terephthalate or polybutylene terephthalate with isophthalic acid, 5-sodium sulfoisophthalic acid, or an aliphatic dicarboxylic acid such as adipic acid as an acid component may also be used.

An artificial blood vessel is a medical device to be used to replace a blood vessel in a living body in a pathological state such as arteriosclerosis, or forming a bypass or shunt. Examples of the material of an artificial blood vessel include fabrics, polytetrafluoroethylene, biomaterials, and synthetic polymer materials. From the viewpoint of simply giving antithrombogenicity, fabrics are preferred.

The antithrombogenicity is a property which prevents blood coagulation, and suppresses thrombus formation. Examples of the method of giving antithrombogenicity include application of heparin or a heparin derivative to the surface of the material.

An example of the index for evaluation of the endothelium-forming ability of an artificial blood vessel is the endothelialization rate. The endothelialization rate can be calculated as follows.

An artificial blood vessel transplanted to an animal blood vessel is removed, and the endothelial cell layer adhering to the inner surface is observed for a pathological specimen. The endothelialization rate can be calculated according to Equation (4).

$$\text{Endothelialization rate (\%)} = L1/L2 \times 100 \quad (4)$$

L1: Longitudinal length of the endothelial cell layer (cm)
L2: Longitudinal length of the artificial blood vessel (cm)

Examples of the animal to which the artificial blood vessel is to be transplanted include mice, rats, dogs, monkeys, pigs, cows, and sheep.

The period of transplantation of the artificial blood vessel is preferably 1 day to 3 years, more preferably 1 week to 1 year, still more preferably 2 weeks to 6 months.

The properties of the block copolymer with which the molded article is coated can be analyzed as follows. For example, the block copolymer is immersed in a solvent such as chloroform, and the resulting extract is dried to obtain a solid, followed by subjecting the solid to measurement such as those described in Measurement Examples 1 to 5.

The block copolymer may be a linear polymer in which the block copolymer units are linearly linked to each other, or may be a branched polymer in which the block copolymer units are linked to form branches.

The block copolymer is represented by General Formula (I).

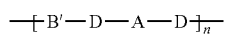
(I)

wherein
A represents a polyhydroxyalkanoic acid block; B represents a polyalkylene glycol block; C represents a linker molecule containing two or more carboxyl groups; and D represents C or a single bond;
B' represents B or a block of two or more Bs linked to each other through C(s) (with the proviso that the molecule necessarily contains a block of two or more Bs linked to each other through C(s)); and
n represents an integer of 1 or more.

The block copolymer represented by General Formula (I) can be synthesized by, for example,
two-block condensation of
a polyhydroxyalkanoic acid block, and
a polyalkylene glycol block having a hydroxyl group at one end and a carboxyl group at the other end; or
three-block condensation of
a polyhydroxyalkanoic acid block,
a polyalkylene glycol block having hydroxyl groups at both ends, and
a polyalkylene glycol block having carboxyl groups at both ends.

When the polyhydroxyalkanoic acid block is a three-component random copolymer composed of repeat units derived from monomers of lactic acid, glycolic acid, and caprolactone, A in General Formula (I) is represented by General Formula (II). It should be noted that General Formula (II) shows a list of the repeat units in the random copolymer.

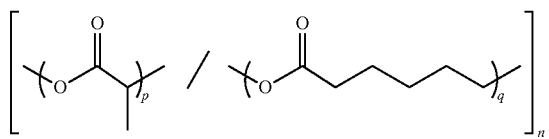
(II)

wherein p, q, r, and n each represent an integer of 1 or more.

When the polyhydroxyalkanoic acid block is a two-component random copolymer composed of repeat units derived from monomers of lactic acid and caprolactone, A in General Formula (I) is represented by General Formula (III). It should be noted that General Formula (III) shows a list of the repeat units in the random copolymer.

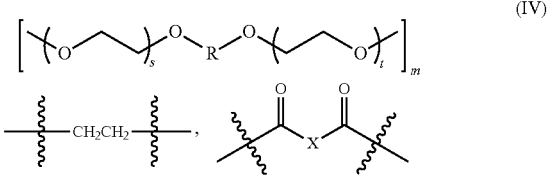
(III)

wherein p, q, and n each represent an integer of 1 or more.

When the polyalkylene glycol block is composed of repeat units derived from ethylene glycol, B in General Formula (I) is represented by General Formula (IV).

(IV)

wherein s, t, and m each represent an integer of 1 or more, and X represents a structure derived from a linker molecule containing two or more carboxyl groups (with the proviso that the molecule necessarily contains B containing X).

When, for example, sebacic acid is used as the linker molecule containing two or more carboxyl groups, X in General Formula (IV) is $(CH_2)_8$.

The polyalkylene glycol having a hydroxyl group at one end and a carboxyl group at the other end, and the polyalkylene glycol having carboxyl groups at both ends, can be synthesized as described above by preliminarily reacting a linker molecule containing two or more carboxyl groups with a polyalkylene glycol (having hydroxyl groups at both ends).

The polyhydroxyalkanoic acid block and the block copolymer can be synthesized by, for example, a method in which cyclic monomers are subjected to ring-opening polymerization in the presence of an initiator and a catalyst (ring-opening polymerization method), a method in which both ends of a block copolymer are bound to the same or different block copolymers, one molecule at a time, through their ends in the presence of a catalyst and/or condensing agent (multimerization method), or a method in which the ring-opening polymerization method and the multimerization method are combined.

Examples of the cyclic monomers include D,L-lactide, L-lactide, glycolide, D,L-lactide-co-glycolide, L-lactide-co-glycolide, ε-caprolactone, γ-butyrolactone, δ-valerolactone, ε-caprolactone-co-lactic acid, and ε-caprolactone-co-glycolic acid-co-lactic acid.

As the catalyst for the production by the ring-opening polymerization method, ordinary polymerization catalysts such as germanium-based catalysts, titanium-based catalysts, antimony-based catalysts, and tin-based catalysts may be used. Specific examples of such polymerization catalysts include stannous octoate, antimony trifluoride, zinc powder, dibutyltin oxide, and tin oxalate. The method of adding the catalyst to the reaction system is not limited. It is preferred to employ a method in which the catalyst is added, upon the feeding of the raw material, in a state where the catalyst is dispersed in the raw material, or a method in which the catalyst is added in a dispersion-treated state at the beginning of the reduction of the pressure. The amount of the catalyst used is preferably 0.01 to 3% by weight, more preferably 0.05 to 1.5% by weight, in terms of the metal atoms with respect to the total amount of monomers used.

Examples of metal catalysts for the production by the multimerization method include metal alkoxides, metal halides, organic carboxylic acid salts, carbonic acid salts, sulfuric acid salts, and oxides, of metals such as tin, titanium, lead, zinc, cobalt, iron, lithium, and rare earths. In view of the polymerization reactivity, tin compounds are preferred. Examples of the tin compounds that may be used include tin powder, tin(II) chloride, tin(IV) chloride, tin(II) bromide, tin(IV) bromide, ethoxytin(II), t-butoxytin(IV), isopropoxytin(IV), tin(II) acetate, tin(IV) acetate, tin(II) octylate, tin(II) laurate, tin(II) myristate, tin(II) palmitate, tin(II) stearate, tin(II) oleate, tin(II) linoleate, tin(II) acetylacetonate, tin(II) oxalate, tin(II) lactate, tin(II) tartrate, tin(II) pyrophosphate, tin(II) p-phenolsulfonate, tin(II) bis(methanesulfonate), tin(II) sulfate, tin(II) oxide, tin(IV) oxide, tin(II) sulfide, tin(IV) sulfide, dimethyltin(IV) oxide, methylphenyltin(IV) oxide, dibutyltin(IV) oxide, dioctyltin(IV) oxide, diphenyltin(IV) oxide, tributyltin oxide, triethyltin(IV) hydroxide, triphenyltin(IV) hydroxide, tributyltin hydride, monobutyltin(IV) oxide, tetramethyltin(IV), tetraethyltin(IV), tetrabutyltin(IV), dibutyldiphenyltin(IV), tetraphenyltin(IV), tributyltin(IV) acetate, triisobutyltin(IV) acetate, triphenyltin(IV) acetate, dibutyltin diacetate, dibutyltin dioctoate, dibutyltin(IV) dilaurate, dibutyltin(IV) maleate, dibutyltin bis(acetylacetonate), tributyltin(IV) chloride, dibutyltin dichloride, monobutyltin trichloride, dioctyltin dichloride, triphenyltin(IV) chloride, tributyltin sulfide, tributyltin sulfate, tin(II) methanesulfonate, tin(II) ethanesulfonate, tin(II) trifluoromethanesulfonate, ammonium hexachlorostannate(IV), dibutyltin sulfide, diphenyltin sulfide, triethyltin sulfate, and tin(II) phthalocyanine.

Examples of non-metal catalysts and condensing agents for the production by the multimerization method include 4,4-dimethylaminopyridine, p-toluenesulfonic acid 4,4-dimethylaminopyridinium, 1-[3-(dimethylamino)propyl]-3-ethylcarbodiimide, 1-ethyl-3-(3-dimethylaminopropyl)carbodiimide hydrochloride, N,N'-dicyclohexylcarbodiimide, N,N'-diisopropylcarbodiimide, N,N'-carbonyldiimidazole, 1,1'-carbonyldi(1,2,4-triazole), 4-(4,6-dimethoxy-1,3,5-triazin-2-yl)-4-methylmorpholinium=chloride n hydrate, trifluoromethanesulfonic acid (4,6-dimethoxy-1,3,5-triazin-2-yl)-(2-octoxy-2-oxoethyl)dimethyl ammonium, 1H-benzotriazol-1-yloxytris(dimethylamino)phosphonium hexafluorophosphate, 1H-benzotriazol-1-yloxytripyrrolidino phosphonium hexafluorophosphate, (7-azabenzotriazol-1-yloxy)tripyrrolidinophosphonium hexafluorophosphate, chlorotripyrrolidinophosphonium hexafluorophosphate, bromotris(dimethylamino)phosphonium hexafluorophosphate, 3-(diethoxyphosphoryloxy)-1,2,3-benzotriazin-4(3H)-one, O-(benzotriazol-1-yl)-N,N,N',N'-tetramethyluronium hexafluorophosphate, O-(7-azabenzotriazol-1-yl)-N,N,N',N'-tetramethyluronium hexafluorophosphate, O-(N-succinimidyl)-N,N,N',N'-tetramethyluronium tetrafluoroborate, O-(N-succinimidyl)-N,N,N',N'-tetramethyluronium hexafluorophosphate, O-(3,4-dihydro-4-oxo-1,2,3-benzotriazin-3-yl)-N,N,N',N'-tetramethyluronium tetrafluoroborate, S-(1-oxide-2-pyridyl)-N,N,N',N'-tetramethylthiuronium tetrafluoroborate, O-[2-oxo-1(2H)-pyridyl]-N,N,N',N'-tetramethyluronium tetrafluoroborate, {{[(1-cyano-2-ethoxy-2-oxoethylidene)amino]oxy}-4-morpholinomethylene} dimethylammonium hexafluorophosphate, 2-chloro-1,3-dimethylimidazolinium hexafluorophosphate, 1-(chloro-1-pyrrolidinylmethylene) pyrrolidinium hexafluorophosphate, 2-fluoro-1,3-dimethylimidazolinium hexafluorophosphate, and fluoro-N,N,N',N'-tetramethylformamidinium hexafluorophosphate.

When the polymerization reaction has a living nature, that is, where the polymerization reaction can be continuously initiated from the end of the polymer, the multimerization can be achieved by repeating the operation of further adding monomers to the block copolymer solution after completion of the polymerization reaction.

Alternatively, the multimerization of the block copolymers may be carried out through a linker(s) as long as the mechanical properties of the block copolymers are not affected. In particular, by using a linker containing a plurality of carboxyl groups or a plurality of hydroxyl groups, for example, by using 2,2-bis(hydroxymethyl)propionic acid, a branched block copolymer containing the linker as a branch point can be synthesized.

The "repeat unit" means, in principle, a repeating unit having a chemical structure derived from a monomer in the chemical structure of a block copolymer obtained by polymerizing two or more kinds of monomers including the monomer.

For example, when lactic acid (CH$_3$CH(OH)COOH) and the caprolactone represented by Chemical Formula (IX) (ε-caprolactone) are polymerized to prepare a co-block copolymer of the lactic acid and the caprolactone, the repeat unit derived from the lactic acid has the structure represented by Chemical Formula (X), and the repeat unit derived from the caprolactone has the structure represented by Chemical Formula (XI).

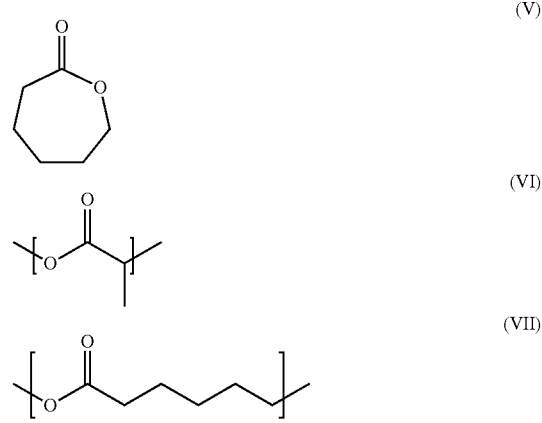

Exceptionally, when a dimer such as lactide is used as the monomer, the "repeat unit" means one of the two repeat structures derived from the dimer. For example, when the dilactide represented by Chemical Formula (XII) (L-(-)-lactide) and caprolactone are polymerized, a structure composed of two repeated structures represented as a dilactide residue is formed in the chemical structure of the block copolymer. In such an example, one of the lactic acid units is regarded as a "repeat unit", and formation of two "repeat units", that is, two lactic acid residues, derived from the dilactide is assumed.

EXAMPLES

Our block copolymers are described below in detail by way of Examples and Comparative Examples, but this disclosure is not limited thereto.

Measurement Example 1: Measurement of Mass Ratio of Polyalkylene Glycol by Nuclear Magnetic Resonance (NMR)

A purified block copolymer was dissolved in deuterated chloroform, and measurement by 1H-NMR was carried out to calculate the molar ratios of lactic acid residues, caprolactone residues, and ethylene glycol residues in the copolymer, and the resulting molar ratios were converted to the mass ratio. The results are shown in Table 3.

Apparatus name: JNM-EX270 (manufactured by JEOL LTD.)
Solvent: deuterated chloroform
Measurement temperature: room temperature In the calculation of the molar ratio of each kind of residues, for example, for the lactic acid residues, the hydrogen atom at the α-position, which is in the methine group, is characteristic (chemical shift value, about 5.2 ppm); for the caprolactone residues, the hydrogen atom at the α-position, which is in the methylene group, is characteristic (chemical shift value, about 2.3 ppm); and, for the ethylene glycol residues, the four hydrogen atoms of the ethylene group (chemical shift value, about 3.6 ppm) are characteristic. Based on the integrated value of the signal that appears at the chemical shift for each of these characteristic hydrogen atoms, each molar ratio can be calculated.

Measurement Example 2: Measurement of Value χ by Differential Scanning calorimetry (DSC)

A purified block copolymer was dried under reduced pressure (100 Pa) at room temperature for one day and night. Thereafter, the block copolymer was dissolved in chloroform at a weight concentration of 5%, and the resulting solution was transferred into a Teflon (registered trademark) petri dish, followed by allowing the solution to dry at normal pressure and room temperature for one day and night. The resulting product was dried under reduced pressure (100 Pa) at room temperature for one day and night to obtain a polymer film having a thickness of 100 μm±50 μm. The polymer film was taken into an aluminum PAN, and subjected to measurement using a differential scanning calorimeter (EXTAR 6000, manufactured by Seiko Instruments Inc.) by the DSC method according to Conditions A to calculate the heat of fusion. The $\chi 1$ was calculated according to Equation 5, and the $\chi 2$ was calculated according to Equation (6).

$\chi 1$=(heat of fusion per unit weight of ethylene glycol residues in copolymer)/{(heat of fusion per unit weight of homopolymer composed only of ethylene glycol residues)×(weight fraction of ethylene glycol residues in copolymer)}×100   (5)

wherein the heat of fusion per unit weight of homopolymer composed only of ethylene glycol residues is 197 J/g.

$\chi 2$=(heat of fusion per unit weight of lactic acid residues in copolymer)/{(heat of fusion per unit weight of homopolymer composed only of lactic acid residues)×(weight fraction of lactic acid residues in copolymer)}×100   (6)

wherein the heat of fusion per unit weight of homopolymer composed only of lactic acid residues is 93 J/g.

Conditions A
Instrument name: EXSTAR 6000 (manufactured by Seiko Instruments Inc.)
Temperature conditions: 25° C.→250° C. (10° C./min)
Standard substance: α-alumina

Measurement Example 3: Tensile Test

A purified block copolymer was dried under reduced pressure (100 Pa) at room temperature for one day and night. Thereafter, the block copolymer was dissolved in chloroform at a weight concentration of 5%, and the resulting solution was transferred into a Teflon (registered trademark) petri dish, followed by allowing the solution to dry at normal pressure and room temperature for one day and night. The resulting product was dried under reduced pressure (100 Pa) at room temperature for one day and night to obtain a film composed of the block copolymer.

The resulting film composed of the block copolymer was cut out into a strip shape (50 mm×5 mm×0.1 mm), and set to a Tensilon universal tester RTM-100 (manufactured by Orientec Co., Ltd.) at a chuck distance in the longitudinal direction of 10 mm according to JIS K6251 (2010). Measurement by a tensile test was carried out according to Conditions B to calculate the Young's modulus, maximum-point elongation, and tensile strength.

Conditions B
Apparatus name: Tensilon universal tensile tester RTM-100 (manufactured by Orientec Co., Ltd.)
Initial length: 10 mm
Tensile rate: 500 mm/min
Load cell: 50 N
Number of tests: 5 tests

Measurement Example 4: Degradation Test 1

A purified block copolymer was dried under reduced pressure (100 Pa) at room temperature for one day and night. Thereafter, the block copolymer was dissolved in chloroform at a weight concentration of 5%, and the resulting solution was transferred into a Teflon (registered trademark) petri dish, followed by allowing the solution to dry at normal pressure and room temperature for one day and night. The resulting product was dried under reduced pressure (100 Pa) at room temperature for one day and night to obtain a polymer film having a thickness of 100 μm±50 μm.

The polymer film obtained was cut out into a size of 20 mm×10 mm, and then placed in a plastic tube containing phosphate buffer (10 mL) such that the entire polymer film was immersed. The tube was then shaken in an incubator set to 47° C. Nine days later, the film was removed and washed with ion-exchanged water, and then dried under reduced pressure (100 Pa) at room temperature for one day and night. Thereafter, the film weight of the dried polymer film was measured. According to the Arrhenius' equation, a test at 47° C. was carried out for providing 3-fold accelerated conditions, and the data at Day 9 were regarded as those at Week 4 at 37° C. according to time conversion. As a parameter indicating the degradability, the block copolymer weight (%) at Week 4 was calculated according to Equation (5).

Block copolymer weight (%) at Week 4=100×w/$w_0$   (5)

$w_0$: Dry weight of the film before the test
w: Dry weight of the film after the test

Measurement Example 5: Kink Resistance Test

A loop was formed with a cylindrical body without application of an internal pressure. A tube having a diameter of R (mm) was inserted into the loop, and the loop diameter was gradually reduced. Whether buckling of the cylindrical body occurred or not before the loop diameter reached the tube diameter was observed. When the buckling did not occur, the cylindrical body was judged to have a kink diameter of not more than R (mm).

Measurement Example 6: Measurement of Carbon Nuclear Relaxation Time T1ρ of Carbonyl Carbon by Solid-State NMR A purified block copolymer was dried under reduced pressure (100 Pa) at room temperature for one day and night. Thereafter, the block copolymer was dissolved in chloroform at a weight concentration of 5%, and the resulting solution was transferred into a Teflon (registered trademark) petri dish, followed by allowing the solution to dry at normal pressure and room temperature for one day and night. The resulting product was dried under reduced pressure (100 Pa) at room temperature for one day and night to obtain a polymer film having a thickness of 100 μm±50 μm. The polymer film was filled into a 5-mm-diameter zirconia rotor, and measurement by solid-state NMR was carried out according to Conditions C, to determine the carbon nuclear relaxation time T1ρ of the carbonyl carbon.
Conditions C
  Apparatus name: CMX300 Infinity (manufactured by Chemagnetics)
  Measurement method: CP/MAS method
  Measurement nuclear frequency: 75.2 MHz ($^{13}$C nucleus)
  Spectral width: 30 kHz
  Pulse width: 4.2 pec (90° pulse)
  Pulse repetition time: ACQTM=0.03413 sec, PD=5 sec
  Contact time: 1.0 msec (CP/MAS)
  Monitoring points: 1024
  Data points: 8192
  Standard substance: polydimethylsiloxane (internal standard: 1.56 ppm)
  Temperature: room temperature (about 22° C.)
  Sample rotation number: 5 kHz
  Atmosphere: dry air Among the peaks found by the solid-state NMR, the peak with a chemical shift value of 170±5 ppm was regarded as the peak for the carbonyl carbon of each residue and, from the peak obtained, the carbon nuclear relaxation time T1ρ was determined to obtain the value of the carbon nuclear relaxation time T1ρ of the carbonyl carbon.

Measurement Example 7: Degradation Test 2

A purified block copolymer was dried under reduced pressure (100 Pa) at room temperature for one day and night. Thereafter, the block copolymer was dissolved in chloroform at a weight concentration of 5%, and the resulting solution was transferred into a Teflon (registered trademark) petri dish, followed by allowing the solution to dry at normal pressure and room temperature for one day and night. The resulting product was dried under reduced pressure (100 Pa) at room temperature for one day and night, to obtain a polymer film having a thickness of 100 μm±50 μm.

The polymer film obtained was cut out into a size of 20 mm×10 mm, and then placed in a plastic tube containing human serum (10 mL) (pooled human serum; manufactured by Cosmo Bio Co., Ltd.) containing sodium azide (0.1% by weight) dissolved therein, such that the entire polymer film was immersed. The tube was then shaken in an incubator set to 47° C. Nine days later, the film was removed and washed with ion-exchanged water, and then dried under reduced pressure (100 Pa) at room temperature for one day and night. Thereafter, the dried polymer film was dissolved in chloroform, and passed through a 0.45-μm syringe filter (DISMIC (registered trademark)-13HP, manufactured by ADVANTEC) to remove impurities and the like, followed by performing GPC according to Conditions D to measure the weight average molecular weight of the block copolymer.
Conditions D
  Apparatus name: Prominence (manufactured by Shimadzu Corporation)
  Mobile phase: chloroform (HPLC grade) (manufactured by Wako Pure Chemical Industries, Ltd.)
  Flow rate: 1 mL/min
  Column: TSKgel (registered trademark) GMHHR-M (7.8 mm (diameter)×300 mm, manufactured by Tosoh Corporation)
  Detector: UV (254 nm), RI
  Column, detector temperature: 35° C.
  Standard substance: polystyrene According to the Arrhenius' equation, a test at 47° C. was carried out for providing 3-fold accelerated conditions, and the data at Day 9 were regarded as those at Week 4 at 37° C. according to time conversion. As a parameter indicating the degradability, the block copolymer weight average molecular weight (%) at Week 4 was calculated according to Equation (8).

$$\text{Block copolymer weight average molecular weight (\%) at Week 4} = 100 \times M/M_0 \quad (6)$$

$M_0$: Weight average molecular weight of the film before the test
$M$: Weight average molecular weight of the film after the test Example 1

In a separable flask, 50.0 g of L-lactide (PURASORB (registered trademark) L, manufactured by PURAC) and 38.5 mL of ε-caprolactone (manufactured by Wako Pure Chemical Industries, Ltd.) were taken as monomers. These were placed under an argon atmosphere, and 0.29 g of tin(II) octylate (manufactured by Wako Pure Chemical Industries, Ltd.) as a catalyst dissolved in 14.5 mL of toluene (superdehydrated) (manufactured by Wako Pure Chemical Industries, Ltd.), and 90 μL of ion-exchanged water as an initiator were added thereto, followed by performing promoter reaction at 90° C. for 1 hour, and then performing copolymerization reaction at 150° C. for 6 hours, to obtain crude polyhydroxyalkanoic acid.

The resulting crude polyhydroxyalkanoic acid was dissolved in 100 mL of chloroform, and then added dropwise to 1400 mL of methanol with stirring, to obtain a precipitate. This operation was repeated three times, and the precipitate was dried under reduced pressure at 70° C., to obtain polyhydroxyalkanoic acid.

A mixture of 11.7 g of the resulting polyhydroxyalkanoic acid, 1.6 g of a polyethylene glycol having hydroxyl groups at both ends (weight average molecular weight, 10,000) (manufactured by Sigma-Aldrich), and 1.7 g of a polyethylene glycol having carboxyl groups at both ends (weight average molecular weight, 10,200) was prepared, and 0.56 g of p-toluenesulfonic acid 4,4-dimethylaminopyridinium (synthesized by the method described in Messmore, Benjamin W. et al., *Journal of the American Chemical Society*, 2004, 126, 14452-14458; the synthesized product was used also in other Examples and Comparative Examples) and 0.20 g of 4,4-dimethylaminopyridine (manufactured by Wako Pure Chemical Industries, Ltd.) as catalysts were added thereto. These were placed under an argon atmosphere, and dissolved in 28 mL of dichloromethane (dehydrated) (manufactured by Wako Pure Chemical Industries, Ltd.). Thereafter, 2.06 g of dicyclohexylcarbodiimide (manufactured by Sigma-Aldrich) as a condensing agent, dissolved in 7 mL of dichloromethane, was added to the resulting solution, and then condensation polymerization was performed at room temperature for 2 days.

To the reaction mixture, 60 mL of chloroform was added, and the resulting mixture was added dropwise to 1000 mL of methanol with stirring, to obtain a precipitate. The precipitate was dissolved in 100 mL of chloroform, and the resulting solution was added dropwise to 1000 mL of methanol with stirring, to obtain a precipitate. This operation was repeated twice to obtain a purified block copolymer of Example 1 as a precipitate.

Example 2

Preparation was carried out by the same method as in Example 1 except that the amount of the polyhydroxyalkanoic acid added was 10.1 g, that the amount of the polyethylene glycol having hydroxyl groups at both ends (weight average molecular weight, 10,000) (manufactured by Sigma-Aldrich) added was 2.5 g, and that the amount of the polyethylene glycol having carboxyl groups at both ends (weight average molecular weight, 10,200) added was 2.5 g. More specifically, a mixture of 10.1 g of a polyhydroxyalkanoic acid obtained by the same method as in Example 1, 2.5 g of a polyethylene glycol having hydroxyl groups at both ends, and 2.5 g of a polyethylene glycol having carboxyl groups at both ends was prepared, and 0.56 g of p-toluenesulfonic acid 4,4-dimethylaminopyridinium and 0.20 g of 4,4-dimethylaminopyridine (manufactured by Wako Pure Chemical Industries, Ltd.) as catalysts were added thereto. These were placed under an argon atmosphere, and dissolved in 28 mL of dichloromethane (dehydrated) (manufactured by Wako Pure Chemical Industries, Ltd.). Thereafter, 2.06 g of dicyclohexylcarbodiimide (manufactured by Sigma-Aldrich) as a condensing agent, dissolved in 7 mL of dichloromethane, was added to the resulting solution, and then condensation polymerization was performed at room temperature for 2 days.

To the reaction mixture, 60 mL of chloroform was added, and the resulting mixture was added dropwise to 1000 mL of methanol with stirring, to obtain a precipitate. The precipitate was dissolved in 100 mL of chloroform, and the resulting solution was added dropwise to 1000 mL of methanol with stirring, to obtain a precipitate. This operation was repeated twice to obtain a purified block copolymer of Example 2 as a precipitate.

Example 3

Preparation was carried out by the same method as in Example 1 except that the amount of the polyhydroxyalkanoic acid added was 6.8 g, that the amount of the polyethylene glycol having hydroxyl groups at both ends (weight average molecular weight, 10,000) (manufactured by Sigma-Aldrich) added was 4.1 g, and that the amount of the polyethylene glycol having carboxyl groups at both ends (weight average molecular weight, 10,200) added was 4.2 g. More specifically, a mixture of 6.8 g of a polyhydroxyalkanoic acid obtained by the same method as in Example 1, 4.1 g of a polyethylene glycol having hydroxyl groups at both ends, and 4.2 g of a polyethylene glycol having carboxyl groups at both ends was prepared, and 0.56 g of p-toluenesulfonic acid 4,4-dimethylaminopyridinium and 0.20 g of 4,4-dimethylaminopyridine (manufactured by Wako Pure Chemical Industries, Ltd.) as catalysts were added thereto. These were placed under an argon atmosphere, and dissolved in 28 mL of dichloromethane (dehydrated) (manufactured by Wako Pure Chemical Industries, Ltd.). Thereafter, 2.06 g of dicyclohexylcarbodiimide (manufactured by Sigma-Aldrich) as a condensing agent, dissolved in 7 mL of dichloromethane, was added to the resulting solution, and then condensation polymerization was performed at room temperature for 2 days.

To the reaction mixture, 60 mL of chloroform was added, and the resulting mixture was added dropwise to 1000 mL of methanol with stirring, to obtain a precipitate. The precipitate was dissolved in 100 mL of chloroform, and the resulting solution was added dropwise to 1000 mL of methanol with stirring, to obtain a precipitate. This operation was repeated twice to obtain a purified block copolymer of Example 3 as a precipitate.

Comparative Example 1

Preparation was carried out by the same method as in Example 1 except that the amount of the polyhydroxyalkanoic acid added was 15.0 g, and that the polyethylene glycol having hydroxyl groups at both ends (weight average molecular weight, 10,000) (manufactured by Sigma-Aldrich) and the polyethylene glycol having carboxyl groups at both ends (weight average molecular weight, 10,200) were not added. More specifically, to 15.0 g of a polyhydroxyalkanoic acid obtained by the same method as in Example 1, 0.56 g of p-toluenesulfonic acid 4,4-dimethylaminopyridinium and 0.20 g of 4,4-dimethylaminopyridine (manufactured by Wako Pure Chemical Industries, Ltd.) as catalysts were added. These were placed under an argon atmosphere, and dissolved in 28 mL of dichloromethane (dehydrated) (manufactured by Wako Pure Chemical Industries, Ltd.). Thereafter, 2.06 g of dicyclohexylcarbodiimide (manufactured by Sigma-Aldrich) as a condensing agent, dissolved in 7 mL of dichloromethane, was added to the resulting solution, and then condensation polymerization was performed at room temperature for 2 days.

To the reaction mixture, 60 mL of chloroform was added, and the resulting mixture was added dropwise to 1000 mL of methanol with stirring, to obtain a precipitate. The precipitate was dissolved in 100 mL of chloroform, and the resulting solution was added dropwise to 1000 mL of methanol with stirring, to obtain a precipitate. This operation was repeated twice to obtain a purified block copolymer of Comparative Example 1 as a precipitate.

Example 4

Preparation was carried out by the same method as in Example 1 except that the amount of the polyhydroxyalkanoic acid added was 13.4 g, that the amount of the polyethylene glycol having hydroxyl groups at both ends (weight average molecular weight, 10,000) (manufactured by Sigma-Aldrich) added was 0.8 g, and that the amount of the polyethylene glycol having carboxyl groups at both ends (weight average molecular weight, 10,200) added was 0.8 g. More specifically, a mixture of 13.4 g of a polyhydroxyalkanoic acid obtained by the same method as in Example 1, 0.8 g of a polyethylene glycol having hydroxyl groups at both ends, and 0.8 g of a polyethylene glycol having carboxyl groups at both ends was prepared, and 0.56 g of p-toluenesulfonic acid 4,4-dimethylaminopyridinium and 0.20 g of 4,4-dimethylaminopyridine (manufactured by Wako Pure Chemical Industries, Ltd.) as catalysts were added thereto. These were placed under an argon atmosphere, and dissolved in 28 mL of dichloromethane (dehydrated) (manufactured by Wako Pure Chemical Industries, Ltd.). Thereafter, 2.06 g of dicyclohexylcarbodiimide (manufactured by Sigma-Aldrich) as a condensing agent, dissolved in 7 mL of dichloromethane, was added to the resulting solution, and then condensation polymerization was performed at room temperature for 2 days.

To the reaction mixture, 60 mL of chloroform was added, and the resulting mixture was added dropwise to 1000 mL of methanol with stirring, to obtain a precipitate. The precipitate was dissolved in 100 mL of chloroform, and the resulting solution was added dropwise to 1000 mL of methanol with stirring, to obtain a precipitate. This operation was repeated twice to obtain a purified block copolymer of Example 4 as a precipitate.

Comparative Example 2

Preparation was carried out by the same method as in Example 1 except that the amount of the polyhydroxyalkanoic acid added was 3.5 g, that the amount of the polyethylene glycol having hydroxyl groups at both ends (weight average molecular weight, 10,000) (manufactured by Sigma-Aldrich) added was 5.7 g, and that the amount of the polyethylene glycol having carboxyl groups at both ends (weight average molecular weight, 10,200) added was 5.8 g. More specifically, a mixture of 3.5 g of a polyhydroxyalkanoic acid obtained by the same method as in Example 1, 5.7 g of a polyethylene glycol having hydroxyl groups at both ends, and 5.8 g of a polyethylene glycol having carboxyl groups at both ends was prepared, and 0.56 g of p-toluenesulfonic acid 4,4-dimethylaminopyridinium and 0.20 g of 4,4-dimethylaminopyridine (manufactured by Wako Pure Chemical Industries, Ltd.) as catalysts were added thereto. These were placed under an argon atmosphere, and dissolved in 28 mL of dichloromethane (dehydrated) (manufactured by Wako Pure Chemical Industries, Ltd.). Thereafter, 2.06 g of dicyclohexylcarbodiimide (manufactured by Sigma-Aldrich) as a condensing agent, dissolved in 7 mL of dichloromethane, was added to the resulting solution, and then condensation polymerization was performed at room temperature for 2 days.

To the reaction mixture, 60 mL of chloroform was added, and the resulting mixture was added dropwise to 1000 mL of methanol with stirring, to obtain a precipitate. The precipitate was dissolved in 100 mL of chloroform, and the resulting solution was added dropwise to 1000 mL of methanol with stirring, to obtain a precipitate. This operation was repeated twice to obtain a purified block copolymer of Comparative Example 2 as a precipitate.

Comparative Example 3: Block Copolymer Represented by General Formula (A)

In a separable flask, 50.0 g of L-lactide (PURASORB (registered trademark) L, manufactured by PURAC) and 38.5 mL of ε-caprolactone (manufactured by Wako Pure Chemical Industries, Ltd.) were taken as monomers. These were placed under an argon atmosphere, and 0.29 g of tin(II) octylate (manufactured by Wako Pure Chemical Industries, Ltd.) as a catalyst dissolved in 14.5 mL of toluene (super-dehydrated) (manufactured by Wako Pure Chemical Industries, Ltd.), and 26.8 g of a polyethylene glycol having hydroxyl groups at both ends (weight average molecular weight, 10,000) (manufactured by Sigma-Aldrich) as an initiator were added thereto, followed by performing copolymerization reaction at 150° C. for 24 hours, to obtain a crude copolymer.

The resulting crude copolymer was dissolved in 100 mL of chloroform, and then added dropwise to 1400 mL of methanol with stirring, to obtain a precipitate. This operation was repeated three times, and the precipitate was dried under reduced pressure at 70° C., to obtain a block copolymer of Comparative Example 3.

Comparative Example 4: Block Copolymer Represented by General Formula (A)

Preparation was carried out by the same method as in Comparative Example 3 except that the weight average molecular weight of the polyethylene glycol having hydroxyl groups at both ends was 20,000. More specifically, in a separable flask, 50.0 g of L-lactide (PURASORB (registered trademark) L, manufactured by PURAC) and 38.5 mL of ε-caprolactone (manufactured by Wako Pure Chemical Industries, Ltd.) were taken as monomers. These were placed under an argon atmosphere, and 0.29 g of tin(II) octylate (manufactured by Wako Pure Chemical Industries, Ltd.) as a catalyst dissolved in 14.5 mL of toluene (super-dehydrated) (manufactured by Wako Pure Chemical Industries, Ltd.), and 26.8 g of a polyethylene glycol having hydroxyl groups at both ends (weight average molecular weight, 20,000) (manufactured by Sigma-Aldrich) as an initiator were added thereto, followed by performing copolymerization reaction at 150° C. for 24 hours, to obtain a crude copolymer.

The resulting crude copolymer was dissolved in 100 mL of chloroform, and then added dropwise to 1400 mL of methanol with stirring, to obtain a precipitate. This operation was repeated three times, and the precipitate was dried under reduced pressure at 70° C., to obtain a block copolymer of Comparative Example 4.

Comparative Example 5: Block Copolymer Represented by General Formula (A)

Preparation was carried out by the same method as in Comparative Example 3 except that the weight average molecular weight of the polyethylene glycol having hydroxyl groups at both ends was 20,000, and that its amount added was 53.6 g. More specifically, in a separable flask, 50.0 g of L-lactide (PURASORB (registered trademark) L, manufactured by PURAC) and 38.5 mL of ε-caprolactone (manufactured by Wako Pure Chemical Industries, Ltd.) were taken as monomers. These were placed under an argon atmosphere, and 0.29 g of tin(II) octylate (manufactured by Wako Pure Chemical Industries, Ltd.) as a catalyst dissolved in 14.5 mL of toluene (super-dehydrated) (manufactured by Wako Pure Chemical Industries, Ltd.), and 53.6 g of a polyethylene glycol having hydroxyl groups at both ends (weight average molecular weight, 20,000) (manufactured by Sigma-Aldrich) as an initiator were added thereto, followed by performing copolymerization reaction at 150° C. for 24 hours, to obtain a crude copolymer.

The resulting crude copolymer was dissolved in 100 mL of chloroform, and then added dropwise to 1400 mL of methanol with stirring, to obtain a precipitate. This operation was repeated three times, and the precipitate was dried under reduced pressure at 70° C., to obtain a block copolymer of Comparative Example 5.

Comparative Example 6: Block Copolymer Represented by General Formula (B)

The block copolymer obtained in Comparative Example 3 in an amount of 15.0 g, and 0.14 g of sebacic acid were taken, and 0.98 g of p-toluenesulfonic acid 4,4-dimethyl-aminopyridinium and 0.36 g of 4,4-dimethylaminopyridine (manufactured by Wako Pure Chemical Industries, Ltd.) as catalysts were taken. These were placed under an argon atmosphere, and dissolved in 28 mL of dichloromethane (dehydrated) (manufactured by Wako Pure Chemical Industries, Ltd.). Thereafter, 3.69 g of dicyclohexylcarbodiimide (manufactured by Sigma-Aldrich) as a condensing agent, dissolved in 13 mL of dichloromethane, was added to the resulting solution, and then condensation polymerization was performed at room temperature for 2 days.

To the reaction mixture, 60 mL of chloroform was added, and the resulting mixture was added dropwise to 1000 mL of methanol with stirring, to obtain a precipitate. The precipitate was dissolved in 100 mL of chloroform, and the resulting solution was added dropwise to 1000 mL of methanol with stirring, to obtain a precipitate. This operation was repeated twice to obtain a block copolymer of Comparative Example 6 as a precipitate.

Comparative Example 7: Block Copolymer Represented by General Formula (C)

The copolymer obtained in Comparative Example 3 in an amount of 10.2 g, and 4.74 g of a polyethylene glycol having carboxyl groups at both ends (weight average molecular weight, 10,200) were taken, and 0.66 g of p-toluenesulfonic acid 4,4-dimethylaminopyridinium and 0.25 g of 4,4-dimethylaminopyridine (manufactured by Wako Pure Chemical Industries, Ltd.) as catalysts were taken. These were placed under an argon atmosphere, and dissolved in 28 mL of dichloromethane (dehydrated) (manufactured by Wako Pure Chemical Industries, Ltd.). Thereafter, 2.49 g of dicyclohexylcarbodiimide (manufactured by Sigma-Aldrich) as a condensing agent, dissolved in 13 mL of dichloromethane, was added to the resulting solution, and then condensation polymerization was performed at room temperature for 2 days.

To the reaction mixture, 60 mL of chloroform was added, and the resulting mixture was added dropwise to 1000 mL of methanol with stirring, to obtain a precipitate. The precipitate was dissolved in 100 mL of chloroform, and the resulting solution was added dropwise to 1000 mL of methanol with stirring, to obtain a precipitate. This operation was repeated twice to obtain a block copolymer of Comparative Example 7 as a precipitate.

Comparative Example 8: Block Copolymer Represented by General Formula (D)

The polyhydroxyalkanoic acid obtained in Example 1 in an amount of 10.1 g, 4.95 g of a polyethylene glycol having hydroxyl groups at both ends (weight average molecular weight, 10,000) (manufactured by Sigma-Aldrich), and 0.10 g of sebacic acid were taken, and 0.93 g of p-toluenesulfonic acid 4,4-dimethylaminopyridinium and 0.34 g of 4,4-dimethylaminopyridine (manufactured by Wako Pure Chemical Industries, Ltd.) as catalysts were added thereto. These were placed under an argon atmosphere, and dissolved in 28 mL of dichloromethane (dehydrated) (manufactured by Wako Pure Chemical Industries, Ltd.). Thereafter, 3.48 g of dicyclohexylcarbodiimide (manufactured by Sigma-Aldrich) as a condensing agent, dissolved in 13 mL of dichloromethane, was added to the resulting solution, and then condensation polymerization was performed at room temperature for 2 days.

To the reaction mixture, 60 mL of chloroform was added, and the resulting mixture was added dropwise to 1000 mL of methanol with stirring, to obtain a precipitate. The precipitate was dissolved in 100 mL of chloroform, and the resulting solution was added dropwise to 1000 mL of methanol with stirring, to obtain a precipitate. This operation was repeated twice to obtain a block copolymer of Comparative Example 8 as a precipitate.

Comparative Example 9

Preparation was carried out by the same method as in Example 1 except that the amount of the polyhydroxyalkanoic acid added was 10.1 g, that the amount of the polyethylene glycol having hydroxyl groups at both ends (weight average molecular weight, 10,000) (manufactured by Sigma-Aldrich) added was 4.4 g, and that 0.5 g of a polyethylene glycol having carboxyl groups at both ends (weight average molecular weight, 1200) was added instead of adding 1.7 g of the polyethylene glycol having carboxyl groups at both ends (weight average molecular weight, 10,200). More specifically, a mixture of 10.1 g of a polyhydroxyalkanoic acid obtained by the same method as in Example 1, 4.4 g of a polyethylene glycol having hydroxyl groups at both ends (weight average molecular weight, 10,000), and 0.5 g of a polyethylene glycol having carboxyl groups at both ends (weight average molecular weight, 1200) was prepared, and 0.56 g of p-toluenesulfonic acid 4,4-dimethylaminopyridinium and 0.20 g of 4,4-dimethylaminopyridine (manufactured by Wako Pure Chemical Industries, Ltd.) as catalysts were added thereto. These were placed under an argon atmosphere, and dissolved in 28 mL of dichloromethane (dehydrated) (manufactured by Wako Pure Chemical Industries, Ltd.). Thereafter, 2.06 g of dicyclohexylcarbodiimide (manufactured by Sigma-Aldrich) as a condensing agent, dissolved in 7 mL of dichloromethane, was added to the resulting solution, and then condensation polymerization was performed at room temperature for 2 days.

To the reaction mixture, 60 mL of chloroform was added, and the resulting mixture was added dropwise to 1000 mL of methanol with stirring, to obtain a precipitate. The precipitate was dissolved in 100 mL of chloroform, and the resulting solution was added dropwise to 1000 mL of methanol with stirring, to obtain a precipitate. This operation was repeated twice to obtain a purified block copolymer of Comparative Example 9 as a precipitate.

For Examples 1 to 4 and Comparative Examples 1 and 2, the amount of the polyhydroxyalkanoic acid added and the amounts of the polyethylene glycols added are shown in Table 1.

TABLE 1

|  | Polyhydroxy-alkanoic acid (g) | Polyethylene glycol having hydroxyl groups at both ends (g) | Polyethylene glycol having carboxyl groups at both ends (g) |
| --- | --- | --- | --- |
| Example 1 | 11.7 | 1.6 | 1.7 |
| Example 2 | 10.1 | 2.5 | 2.5 |

TABLE 1-continued

|  | Polyhydroxy-alkanoic acid (g) | Polyethylene glycol having hydroxyl groups at both ends (g) | Polyethylene glycol having carboxyl groups at both ends (g) |
|---|---|---|---|
| Example 3 | 6.8 | 4.1 | 4.2 |
| Comparative Example 1 | 15.0 | 0.0 | 0.0 |
| Example 4 | 13.4 | 0.8 | 0.8 |
| Comparative Example 2 | 3.5 | 5.7 | 5.8 |

For Comparative Examples 3 to 5, the weight average molecular weight of the polyethylene glycol block and its amount added are shown in Table 2.

TABLE 2

|  | Weight average molecular weight | Amount added (g) |
|---|---|---|
| Comparative Example 3 | 10000 | 26.8 |
| Comparative Example 4 | 20000 | 26.8 |
| Comparative Example 5 | 20000 | 53.6 |

The measurement results on the block copolymers obtained in Examples 1 to 4 and Comparative Examples 1 to 9 are shown in Tables 3 to 5.

TABLE 3

|  | Mass ratio of polyalkylene glycol (%) | Mass ratio of polycaprolactone (%) | c 1 | c 2 | c | Block copolymer weight at Week 4 (%) | Young's modulus (MPa) | Maximum-point elongation (%) | Tensile strength (MPa) |
|---|---|---|---|---|---|---|---|---|---|
| Example 1 | 22 | 33 | 50.1 | 16.0 | 802 | 92 | 5.3 | 1322 | 16.2 |
| Example 2 | 28 | 30 | 67.9 | 13.9 | 941 | 84 | 9.8 | 1355 | 10.0 |
| Example 3 | 49 | 21 | 84.1 | 18.0 | 1513 | 69 | 33.6 | 1406 | 13.7 |
| Comparative Example 1 | 0 | 42 | — | — | — | 100 | 3.4 | 1071 | 29.9 |
| Example 4 | 11 | 37 | 1.4 | 19.9 | 28 | 99 | 5.1 | 1024 | 21.1 |
| Comparative Example 2 | 67 | 10 | — | — | — | — | 53.1 | 36 | 7.8 |
| Comparative Example 3 | 22 | 34 | 44.9 | 4.9 | 221 | — | 13.9 | 59 | 2.1 |
| Comparative Example 4 | 15 | 37 | 35.3 | 10.0 | 352 | — | 6.8 | 102 | 2.0 |
| Comparative Example 5 | 33 | 29 | 66.6 | 5.7 | 377 | — | 11.7 | 68 | 2.2 |
| Comparative Example 6 | 16 | 36 | 20.9 | 2.0 | 41 | — | 4.6 | 179 | 1.8 |
| Comparative Example 7 | 28 | 33 | 56.2 | 2.2 | 125 | — | 26.1 | 54 | 4.5 |
| Comparative Example 8 | 24 | 34 | 62.1 | 0.3 | 16 | — | 13.1 | 1453 | 3.3 |
| Comparative Example 9 | 25 | 36 | 59.8 | 3.1 | 185 | — | 4.5 | 1682 | 4.7 |

TABLE 4

|  | Weight average molecular weight of polyalkylene glycol | | Weight average molecular weight of block copolymer at Week 4 (%) |
|---|---|---|---|
|  | Hydroxyl groups at both ends | Carboxyl groups at both ends | |
| Example 1 | 10000 | 10200 | 62 |
| Example 2 | 10000 | 10200 | 46 |
| Example 3 | 10000 | 10200 | 31 |
| Comparative Example 1 | — | — | 90 |
| Example 4 | 10000 | 10200 | 81 |
| Comparative Example 2 | 10000 | 10200 | — |
| Comparative Example 3 | 10000 | — | — |
| Comparative Example 4 | 20000 | — | — |
| Comparative Example 5 | 20000 | — | — |
| Comparative Example 6 | 10000 | — | — |
| Comparative Example 7 | 10000 | 10200 | — |
| Comparative Example 8 | 10000 | — | — |
| Comparative Example 9 | 10000 | 1200 | — |

TABLE 5

|  | T1r (ms) | | | | | |
|---|---|---|---|---|---|---|
|  | 170 ppm | 70 ppm | 66 ppm | 34 ppm | 28 ppm | 18 ppm |
| Example 1 | 8 | 3.1 | 1.0 | 1.5 | 1.9 | 4.8 |
| Example 2 | 16 | 7.6 | 1.2 | 1.8 | 2.1 | 7.7 |
| Example 3 | 7 | 2.7 | 0.9 | 1.4 | 1.8 | 4.4 |
| Comparative Example 1 | — | — | — | — | — | — |
| Example 4 | 5 | 1.5 | 1.0 | 1.2 | 1.4 | 2.7 |
| Comparative Example 2 | — | — | — | — | — | — |
| Comparative Example 3 | 126 | 26.2 | 9.4 | 2.8 | 2.7 | 46.1 |
| Comparative Example 4 | 112 | 23.0 | 8.5 | 2.6 | 2.7 | 38.2 |
| Comparative Example 5 | 150 | 30.1 | 11.2 | 3.0 | 3.3 | 51.5 |
| Comparative Example 6 | 79 | 18.1 | 5.9 | 2.5 | 2.8 | 30.6 |
| Comparative Example 7 | 49 | 12.1 | 3.4 | 2.1 | 2.9 | 18.2 |
| Comparative Example 8 | 24 | 12.7 | 1.7 | 2.5 | 2.9 | 11.6 |
| Comparative Example 9 | 22 | 7.0 | 1.9 | 1.5 | 1.8 | 10.1 |

Example 5

The block copolymer of Example 1 was dissolved in chloroform, to prepare a solution having a weight concentration of 20%. By application of the solution to a water-permeable cylindrical body (10 cm in length, 3 mm in inner diameter) composed of polyester fibers, a 100-μm coating layer was formed to obtain a coated cylindrical body of Example 5. As a result of measurement according to the method described in Measurement Example 5, the kink diameter was found to be not more than 8 mm.

Subsequently, the coated cylindrical body of Example 5 was cut to a length of 3 cm, and the water permeability was measured according to ISO7198 by dividing the amount of water (mL) that flowed out to the outside of the cylindrical body upon application of a pressure of 16 kPa to the inner surface of the cylindrical body, by the unit area ($cm^2$) and the unit time (min). As a result, the water permeability of the coated cylindrical body of Example 5 was found to be 0 ($mL/cm^2/min$).

Example 6

Preparation was carried out by the same method as in Example 5 except that the block copolymer of Example 2 was used. More specifically, the block copolymer of Example 2 was dissolved in chloroform, to prepare a solution having a weight concentration of 20%. By application of the solution to a water-permeable cylindrical body (10 cm in length, 3 mm in inner diameter) composed of polyester fibers, a 100-μm coating layer was formed to obtain a coated cylindrical body of Example 6. As a result of measurement of the kink diameter of the coated cylindrical body of Example 6 according to Measurement Example 5, the kink diameter was found to be not more than 8 mm. As a result of measurement of the water permeability according to ISO7198 by dividing the amount of water (mL) that flowed out to the outside of the cylindrical body upon application of a pressure of 16 kPa to the inner surface of the cylindrical body, by the unit area ($cm^2$) and the unit time (min), the water permeability of the coated cylindrical body of Example 6 was found to be 0 ($mL/cm^2/min$).

Example 7

Preparation was carried out by the same method as in Example 5 except that the block copolymer of Example 3 was used. More specifically, the block copolymer of Example 3 was dissolved in chloroform, to prepare a solution having a weight concentration of 20%. By application of the solution to a water-permeable cylindrical body (10 cm in length, 3 mm in inner diameter) composed of polyester fibers, a 100-μm coating layer was formed to obtain a coated cylindrical body of Example 7. As a result of measurement of the kink diameter of the coated cylindrical body of Example 7 according to Measurement Example 5, the kink diameter was found to be not more than 14 mm. As a result of measurement of the water permeability according to ISO7198 by dividing the amount of water (mL) that flowed out to the outside of the cylindrical body upon application of a pressure of 16 kPa to the inner surface of the cylindrical body, by the unit area ($cm^2$) and the unit time (min), the water permeability of the coated cylindrical body of Example 7 was found to be 0 ($mL/cm^2/min$).

Example 8

Preparation was carried out by the same method as in Example 5 except that the block copolymer of Example 4 was used. More specifically, the block copolymer of Example 4 was dissolved in chloroform, to prepare a solution having a weight concentration of 20%. By application of the solution to a water-permeable cylindrical body (10 cm in length, 3 mm in inner diameter) composed of polyester fibers, a 100-μm coating layer was formed to obtain a coated cylindrical body of Example 8. As a result of measurement of the kink diameter of the coated cylindrical body of Example 8 according to Measurement Example 7, the kink diameter was found to be not more than 8 mm. As a result of measurement of the water permeability according to ISO7198 by dividing the amount of water (mL) that flowed out to the outside of the cylindrical body upon application of a pressure of 16 kPa to the inner surface of the cylindrical body, by the unit area ($cm^2$) and the unit time (min), the water permeability of the coated cylindrical body of Example 8 was found to be 0 ($mL/cm^2/min$).

Test Example 1

The coated cylindrical body of Example 6 was transplanted to the carotid artery of a dog. Three months later, the cylindrical body was removed. As a result of observation of a pathological specimen of the removed cylindrical body, fragmentation of the coating layer due to degradation was found. The endothelialization rate calculated according to Equation 4 for the coated cylindrical body of Example 6 was 63.2%.

Comparative Example 10

Gelatin (manufactured by Nitta Gelatin Inc.) was dissolved in water at 60° C., to prepare a solution having a weight concentration of 30%. The solution, under warming at 40° C., was applied to a water-permeable cylindrical body (3 cm in length, 3 mm in inner diameter) composed of polyester fibers, to form a 100-μm coating layer. The resulting cylindrical body was immersed in 0.2% aqueous glutaraldehyde solution at room temperature for 30 minutes, and then washed, to obtain a coated cylindrical body of Comparative Example 10. The coated cylindrical body of Comparative Example 10 was transplanted to the carotid artery of a dog. Three months later, the cylindrical body was removed. As a result of observation of a pathological specimen of the removed cylindrical body, the coating layer was found to be remaining without fragmentation.

The endothelialization rate calculated according to Equation 4 for the coated cylindrical body of Comparative Example 10 was 47.3%.

INDUSTRIAL APPLICABILITY

Our block copolymer can be used for medical uses such as medical coating materials, vascular embolization materials, suture threads, and DDS carriers.

The invention claimed is:
1. A linear block copolymer comprising a polyalkylene glycol block and a polyhydroxyalkanoic acid block,
wherein
the polyhydroxyalkanoic acid block is a three-component random copolymer composed of repeat units derived from monomers of lactic acid, glycolic acid, and caprolactone, or a two-component random copolymer composed of repeat units derived from monomers of lactic acid and caprolactone;
a mass ratio of a polyalkylene glycol block with respect to a total mass is 10 to 50%;

the block copolymer has a weight average molecular weight of not less than 10,000 and not more than 1,600,000;

the polyalkylene glycol block has a weight average molecular weight of not less than 7,000 and not more than 170,000;

the block copolymer has a maximum-point elongation of not less than 600%;

the carbonyl carbon has a carbon nuclear relaxation time T1ρ of not more than 20 ms; and the linear block copolymer is a block copolymer in which repeat units represented by General Formula below are linearly linked to each other:

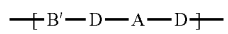

wherein

A represents a polyhydroxyalkanoic acid block; B' represents B or a block of two or more Bs linked to each other through C(s), with the proviso that the molecule necessarily contains a block of two or more Bs linked to each other through C(s); B represents a polyalkylene glycol block; C represents a structure derived from a linker molecule containing two or more carboxyl groups; and D represents C or a single bond; and the repeat units of the linear block copolymer include a first repeat unit and a second repeat unit that is different from the first repeat unit, wherein in the first repeat unit, D between B' and A represents C, and in the second repeat unit, D between B' and A represents single bond.

2. The block copolymer according to claim 1, wherein a mass ratio of the repeat unit derived from caprolactone with respect to the total mass of the block copolymer is 15 to 80%.

3. The block copolymer according to claim 1, wherein A is represented by General Formula (II):

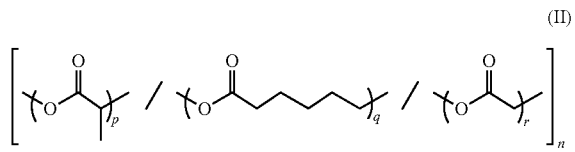

wherein p, q, r, and n each represent an integer of 1 or more.

4. The block copolymer according to claim 1, wherein A is represented by General Formula (III):

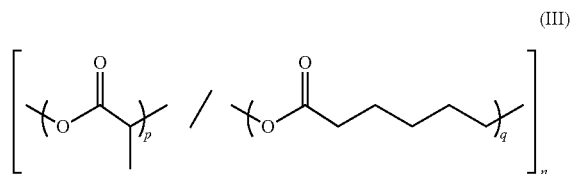

wherein p, q, and n each represent an integer of 1 or more.

5. The block copolymer according to claim 1, wherein B' is represented by General Formula (IV):

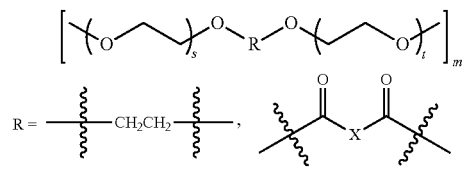

wherein s, t, and m each represent an integer of 1 or more, and X represents a structure derived from a linker molecule containing two or more carboxyl groups, and the linker molecule is selected from the group consisting of dicarboxylic acids, acid halides, acid anhydrides, and esters of the dicarboxylic acids (with the proviso that the molecule necessarily contains B' containing X).

6. A medical material comprising: the block copolymer according to claim 1, and a molded article to be coated with the block copolymer.

7. A medical material comprising: the block copolymer according to claim 2, and a molded article to be coated with the block copolymer.

8. A medical material comprising: the block copolymer according to claim 3, and a molded article to be coated with the block copolymer.

9. A medical material comprising: the block copolymer according to claim 4, and a molded article to be coated with the block copolymer.

10. A medical material comprising: the block copolymer according to claim 5, and a molded article to be coated with the block copolymer.

11. The block copolymer according to claim 5, wherein the dicarboxylic acids are selected from the group consisting of oxalic acid, malonic acid, succinic acid, glutaric acid, adipic acid, pimelic acid, suberic acid, azelaic acid, sebacic acid, malic acid, tartaric acid, and dodecanedioic acid.

12. The block copolymer according to claim 1, wherein the polyalkylene glycol block has a structure derived from a polyethylene glycol having hydroxyl groups at both ends and a polyethylene glycol having carboxyl groups of the linker molecule at both ends.

13. The block copolymer according to claim 1, wherein the caprolactone has an α-carbon nuclear relaxation time T1ρ of not more than 2.0 ms.

14. The block copolymer according to claim 1, wherein the methylene group at the 6-position of the caprolactone has a carbon nuclear relaxation time T1ρ of not more than 1.5 ms.

15. The block copolymer according to claim 1, wherein the methine group of the lactic acid and the methylene group of the ethylene glycol block have a carbon nuclear relaxation time T1ρ of not more than 8.0 ms.

16. A linear block copolymer comprising a polyalkylene glycol block and a polyhydroxyalkanoic acid block, wherein the polyhydroxyalkanoic acid block is a three-component random copolymer composed of repeat units derived from monomers of lactic acid, glycolic acid, and caprolactone, or a two-component random copolymer composed of repeat units derived from monomers of lactic acid and caprolactone;

a mass ratio of a polyalkylene glycol block with respect to a total mass is 10 to 60%;

the block copolymer has a weight average molecular weight of not less than 10,000 and not more than 1,600,000;

The polyalkylene glycol block has a weight average molecular weight of not less than 7,000 and not more than 170,000;

the block copolymer has a maximum-point elongation of not less than 600%;

the carbonyl carbon has a carbon nuclear relaxation time T1ρ of not more than 20 ms; and the linear block copolymer is a block in which repeat units represented by General Formula below are linearly linked to each other:

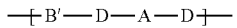

wherein

A represents a polyhydroxyalkanoic acid block; B' is represented by General Formula (IV):

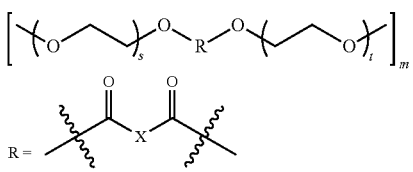

wherein s, t, and m each represent an integer of 1 or more, and X represents a structure derived from a linker molecule selected from the group consisting of oxalic acid, malonic acid, succinic acid, glutaric acid, adipic acid, pimelic acid, suberic acid, azelaic acid, sebacic acid, and dodecanedioic acid;

and D represents R or a single bond.

17. The block copolymer according to claim 1, wherein a mass ratio of the repeat unit derived from caprolactone with respect to the total mass of the block copolymer is 20 to 37%.

18. The block copolymer according to claim 1, wherein the block copolymer has a tensile strength of not less than 9.0 MPa.

19. The block copolymer according to claim 1, wherein the repeat units of the block copolymer comprise a repeat unit represented by General Formula-[B-C-B-C-A]-.

20. The block copolymer according to claim 1, wherein the repeat units of the block copolymer comprise a repeat unit represented by General Formula-[B-C-B-C-A]- and a repeat unit represented by General Formula-[B-C-B-A-C]-.

21. The multiblock copolymer according to claim 1, wherein the repeat units of the block copolymer comprise a repeat unit represented by General Formula-[B-C-B-D-A-D]-.

22. The multiblock copolymer according to claim 1, wherein the multiblock copolymer satisfies Equation (1):

$$\chi = \chi 1 \times \chi 2 > 20 \tag{1}$$

χ1: crystallization rate of the polyalkylene glycol block, which is determined according to the following Equation (2):

$$\chi 1 = \text{(heat of fusion per unit weight of alkylene glycol residues in copolymer)} / \{\text{(heat of fusion per unit weight of homopolymer composed only of alkylene glycol residues)} \times \text{(weight fraction of alkylene glycol residues in copolymer)}\} \times 100 \tag{2};$$

χ2: crystallization rate of a poly-A block, wherein A represents, among repeat units contained in the polyhydroxyalkanoic acid block, a repeat unit whose homopolymer composed of a same repeat unit has a highest crystallization rate among homopolymers, which is determined according to the following Equation (3):

$$\chi 2 = \text{(heat of fusion per unit weight of A-residues in copolymer)} / \{\text{(heat of fusion per unit weight of homopolymer composed only of A-residues)} \times \text{(weight fraction of A-residues in copolymer)}\} \times 100 \tag{3}.$$

23. The multiblock copolymer according to claim 16, wherein the multiblock copolymer satisfies Equation (1):

$$\chi = \chi 1 \times \chi 2 > 20 \tag{1}$$

χ1: crystallization rate of the polyalkylene glycol block, which is determined according to the following Equation (2):

$$x1 = \text{(heat of fusion per unit weight of alkylene glycol residues in copolymer)} / \{\text{(heat of fusion per unit weight of homopolymer composed only of alkylene glycol residues)} \times \text{(weight fraction of alkylene glycol residues in copolymer)}\} \times 100 \tag{2};$$

χ2: crystallization rate of a poly-A block, wherein A represents, among repeat units contained in the polyhydroxyalkanoic acid block, a repeat unit whose homopolymer composed of a same repeat unit has a highest crystallization rate among homopolymers, which is determined according to the following Equation (3):

$$\chi 2 = \text{(heat of fusion per unit weight of A-residues in copolymer)} / \{\text{(heat of fusion per unit weight of homopolymer composed only of A-residues)} \times \text{(weight fraction of A-residues in copolymer)}\} \times 100 \tag{3}.$$

24. The block copolymer according to claim 1, wherein the block copolymer has a tensile strength of not less than 9.0 MPa.

* * * * *